United States Patent
Ochiai et al.

(10) Patent No.: US 6,569,572 B1
(45) Date of Patent: May 27, 2003

(54) LITHIUM BATTERY, POLYMER ELECTROLYTE, ELECTROLYTE MATERIAL, DI(METH)ACRYLIC ESTER, AND DI(METH)ACRYLATE POLYMER

(75) Inventors: Seijiro Ochiai, Takatsuki (JP); Syuichi Izuchi, Takatsuki (JP); Takeshi Ishitoku, Yokohama (JP); Masaharu Shindo, Tokyo (JP); Hidenobu Nogi, Sodegaura (JP)

(73) Assignees: Yuasa Corporation, Takatsuki (JP); Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/529,273

(22) PCT Filed: Aug. 11, 1999

(86) PCT No.: PCT/JP99/04339

§ 371 (c)(1), (2), (4) Date: Apr. 11, 2000

(87) PCT Pub. No.: WO00/10213

PCT Pub. Date: Feb. 24, 2000

(30) Foreign Application Priority Data

Aug. 11, 1998 (JP) .............................. 10-226788
May 10, 1999 (JP) .............................. 11-129215

(51) Int. Cl.$^7$ ........................ H01M 10/40; C07C 69/96
(52) U.S. Cl. ....................... 429/303; 429/317; 558/265; 558/276
(58) Field of Search .............................. 429/303, 317; 558/265, 276

(56) References Cited

U.S. PATENT DOCUMENTS

| 4,783,544 | A | | 11/1988 | Yokoshima et al. ........ 558/267 |
| 5,021,467 | A | | 6/1991 | Yokoshima et al. ........ 522/96 |
| 5,654,112 | A | * | 8/1997 | Itou et al. .............. 429/317 X |
| 6,190,805 | B1 | * | 2/2001 | Takeuchi et al. ......... 429/317 X |
| 6,235,433 | B1 | * | 5/2001 | Amano et al. ............ 429/303 |

FOREIGN PATENT DOCUMENTS

| EP | 207688 | * | 1/1987 |
| JP | 63-94563 | | 4/1988 |
| JP | 5-25353 | | 2/1993 |
| JP | 5-178948 | | 7/1993 |
| JP | 5-178949 | | 7/1993 |
| JP | 5-303980 | | 11/1993 |
| JP | 6-223842 | | 8/1994 |
| JP | 62-207240 | | 9/1997 |
| WO | 98/25275 | * | 6/1998 |

* cited by examiner

*Primary Examiner*—Stephen Kalafut
(74) *Attorney, Agent, or Firm*—Crowell & Moring LLP (57) ABSTRACT

In a lithium battery comprising a positive electrode, a negative electrode and a gel electrolyte; the gel electrolyte is composed of at least an ester-group or ether-group aprotic polar solvent, a lithium salt and a polymeric compound, and the polymeric compound comprises a polymer of at least one compound among those expressed by an equation (I) and an equation (II).

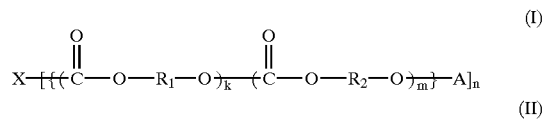

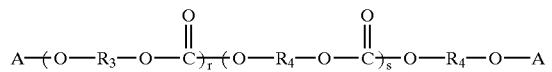

(k: zero or number of 1 or more, m: number of 1 or more, $R_1$:$C_pH_{2p}$, $R_2$:$C_qH_{2q}$, p≠q, p & q: integer of 1 or more, A: $CH_2$=CH—CO— or $CH_2$=C($CH_3$)—CO—, X: n-valent combination group (n: integer ranging from 1 to 4), r: zero or number of 1 or more, s: number of 1 or more, $R_3$: $C_tH_{2t}$, $R_4$: $C_uH_{2u}$, t≠u, t & u: integer of 1 or more).

10 Claims, 4 Drawing Sheets

LITHIUM BATTERY, POLYMER ELECTROLYTE, ELECTROLYTE MATERIAL, DI(METH)ACRYLIC ESTER, AND DI(METH)ACRYLATE POLYMER

BACKGROUND OF THE INVENTION

This invention relates to a lithium battery utilizing a gel electrolyte, and further to a polyelectrolyte, an electrolyte material, a di(metha)-acrylic ester and a di(metha)-acrylate polymer.

With a recent tendency to design a portable electric device into a compact form, a demand for a lithium battery providing a high energy density has been increasing. It is expected to apply this lithium battery to a large-size battery such as for use in an electric vehicle etc. In studies and developments of the battery, it is indispensable to establish various technologies for increasing a high energy density and battery capacity, and improving a stability.

Incidentally, a battery utilizing the polymeric solid electrolyte provides high reliability and safety owing to its non-leakage property of electrolyte as compared with conventional battery utilizing a liquid electrolyte. In addition, this battery enables thinning of film, simplification of package and decrease in weight. For this reason, a large expectation is placed on the polymeric solid electrolyte. As for the polymeric solid electrolyte, those described in the Published Patent Application (KOKAI) No. 5-25353 and the Published Patent Application (KOKAI) No. 6-223842 are well known. However, the polymeric solid electrolyte is generally composed of a composite of polymeric compound and alkali metal salt, and its ion conduction mechanism is one which utilizes a molecular motion of the polymeric compound. For this reason, the polymeric solid electrolyte has, in general, a small ion conductivity as compared with the liquid electrolyte. The battery using the polymeric solid electrolyte has included such a problem that its charge/discharge current density has been limited as compared with the battery using the liquid electrolyte.

Accordingly, it is desired to develop a polymeric solid electrolyte having a high ion conductivity.

Under such circumstances, as described in the Published Patent Application (KOKAI) No. 63-94563, a polyelectrolyte having a comparatively high ion conductivity can be obtained in such a way that a crosslink polyalkylene oxide is used for the polymeric compound and an organic solvent is contained in the composite of the polymeric compound and the alkali metal salt. Such a polyelectrolyte containing the organic solvent is called as a gel electrolyte and its application to a lithium battery is actively examined at present. On the other hand, gel electrolytes are also examined which utilize polyacrylonitrile (PAN), polyvinylidene fluoride (PVdF) or similar compound of them as the polymeric compound, in place of the crosslink polyalkylene oxide. However, the gel electrolyte using the PAN can not maintain its state of film at high temperature because the polymeric compound is apt to become fluidic with an increase in its temperature, so that it is inferior in its form stability at high temperature. The gel electrolyte using the PVdF is inferior in its liquid electrolyte holding ability because the PVdF presents its slight solubility against the liquid electrolyte. On the contrary, the gel electrolyte using the crosslink polyalkylene oxide as the polymeric compound has a high liquid electrolyte holding ability because the polymeric compound presents its compatibility with the liquid electrolyte, and its form can be maintained over a wide range of temperature because the polymeric compound has a crosslink structure. Namely, the gel electrolyte using the crosslink polyalkylene oxide, when used for the lithium battery, can improve a reliability and safety of battery because the gel electrolyte is superior in the liquid electrolyte holding ability and the form stability.

However, the lithium battery equipped with the gel electrolyte using the crosslink polyalkylene oxide is not superior in its low-temperature property and high-rate property during charging and discharging, and its battery performance is inferior to those of the lithium battery equipped with the gel electrolyte using the PAN and the PVdF. A cause of this problem may be supposed as follows.

In the gel electrolyte, lithium ion preferentially coordinates with the crosslink polyalkylene oxide forming the polymeric compound as compared with an organic solvent such as a generally used cyclic ester carbonate. This is suggested by a fact that an ether-group solvent having a structure similar to the crosslink polyalkylene oxide has a large possibility to preferentially coordinate with the lithium ion because of a large donor number, as compared with the cyclic ester carbonate etc. Then, since the polymeric compound has an extremely low moving ability as compared with the organic solvent, a moving ability of lithium ion in the gel electrolyte is decreased, when the lithium ion preferentially coordinates with the crosslink polyalkylene oxide forming the polymeric compound rather than the organic solvent.

On the contrary, it can be considered that, in the gel electrolyte using the PAN or PVdF as the polymeric compound, the lithium ion is not restricted by the polymeric compound and the decrease in the moving ability of lithium ion is controlled because a lithium salt is slightly soluble or not soluble to the polymeric compound. As described above, however, the gel electrolyte using the PAN includes such a problem that it is inferior in the form stability at high temperature and the gel electrolyte using the PVdF includes such a problem that it is inferior in the liquid electrolyte holding ability.

SUMMARY OF THE INVENTION

A first object of this application is to provide a lithium battery which is able to improve its reliability and safety, and further to improve its low-temperature property and high-rate property during charging and discharging.

A second object of this application is to provide a polyelectrolyte which is superior in its ion conductivity and also in its electrochemical stability.

A third object of this application is to provide an electrolyte material which is able to compose the polyelectrolyte of the above second object.

A fourth object of this application is to provide a di(metha)-acrylic ester and a di(metha)-acrylate polymer forming an useful novel compound.

In order to accomplish the first object, a first invention of this application is characterized by that, in a lithium battery equipped with a positive electrode, a negative electrode and a gel electrolyte, the gel electrolyte is composed of at least an ester-group or ether-group aprotic polar solvent, a lithium salt and a polymeric compound; and this polymeric compound comprises a polymer of at least one compound among those expressed by an equation (I) and an equation (II).

(k: zero or number of 1 or more, m: number of 1 or more, $R_1$:$C_pH_{2p}$, $R_2$:$C_qH_{2q}$, $p \neq q$, p & q: integer of 1 or more, A: $CH_2=CH-CO-$ or $CH_2=C(CH_3)-CO-$, X: n-valent combination group (n: integer ranging from 1 to 4), r: zero or number of 1 or more, s: number of 1 or more, $R_3$: $C_tH_{2t}$, $R_4$: $C_uH_{2u}$, $t \neq u$, t & u: integer of 1 or more)

According to the lithium battery of this invention, the low-temperature property and high-rate property during charging and discharging can be improved because the gel electrolyte can exert a high lithium ion mobility. A reason of this fact may be considered as follows. The polymer of compound expressed by the equation (I) and the polymer of compound expressed by the equation (II) have structural characteristics inferior in their lithium ion coordination property as compared with the crosslink polyaklylene oxide. These structural characteristics are caused by the number of carbon atom sandwiched by two oxygen atoms. Therefore, in the gel electrolyte of this invention, the lithium ion coordinates to about the same extent with the polymeric compound and the ester-group or ether-group aprotic polar solvent. Consequently, in the gel electrolyte of this invention, a percentage of the lithium ion restricted by the polymeric compound is reduced as compared with a case of the gel electrolyte using the crosslink polyalkylene oxide. Therefore, the gel electrolyte of this invention can exert a high lithium ion mobility as compared with the case of the gel electrolyte using the crosslink polyalkylene oxide.

In addition, the lithium battery of this invention is highly reliable because the gel electrolyte is superior in the liquid electrolyte holding ability. A reason may be considered as follows. The polymer of compound expressed by the equation (I) and the polymer of compound expressed by the equation (II) have structural characteristics superior in its compatibility with the ester-group or ether-group aprotic polar solvent. Therefore, the gel electrolyte of this invention is superior in the liquid electrolyte holding ability.

Further, the lithium battery of this invention has high safety because the gel electrolyte is superior in its form stability. A reason may be considered as follows. The polymer of compound expressed by the equation (I) and the polymer of compound expressed by the equation (II) can maintain their forms over a wide range of temperature because these polymers have the crosslink structure. Therefore, the gel electrolyte of this invention is superior in its form stability.

As the ester-group or ether-group aprotic polar solvent, following solvents may be mentioned: cyclic ester carbonates such as ethylene carbonate and propylene carbonate etc.; cyclic carboxylic esters such as γ-butyrolactone etc.; cyclic ethers such as tetrahydrofuran and 1,3-dioxolan etc.; chain ethers such as 1,2-dimethoxy ethane etc.; chain ester carbonates such as dimethyl carbonate and ethyl methyl carbonate etc.; chain carboxylic ester such as propionic methyl etc. However, they are not limited to these solvents. Further, a solvent may be used which are prepared by mixing two or more kinds of solvents.

$LiPF_6$, $LiBF_4$, $LiN(SO_2CF_3)_2$ and $LiOSO_2CF_3$ etc. may be used for the lithium salt. However, it is not limited to these salts.

Compounds expressed by equations (III) through equation (XI) may be used for the X-group of the equation (I). However, it is not limited to these compounds.

In the lithium battery of this invention, following structures (1) through (4) may be used.

(1) A number-average molecular weight of the compound expressed by the equation (I) ranges from 160 to 100,000.

(2) A number-average molecular weight of the compound expressed by the equation (II) ranges from 228 to 100,000.

When a molecular weight of the compound expressed by the equation (I) and a molecular weight of the compound expressed by the equation (II) are smaller than the above values, a crosslink density of the polymeric compound forming a polymer becomes large and a flexibility of the film composed of the polymeric compound is worsened. In contrast with this, when a molecular weight of the compound expressed by the equation (I) and a molecular weight of the compound expressed by the equation (II) are larger than the above values, the crosslink density of the polymeric compound forming the polymer becomes small and a strength of the film composed of the polymeric compound is worsened.

(3) The polymeric compound is a copolymer of at least one compound among those expressed by the equation (I) and the equation (II), with another monomer. And, a weight content of the compounds expressed by the equation (I) and the equation (II) in the copolymer is larger than or equal to 50 wt %.

When the weight content of the compounds expressed by the equation (I) and the equation (II) in the copolymer is smaller than 50 wt %, structural characteristics of the compounds expressed by the equation (I) and the equation (II) do not present themselves as in case of characteristics of the copolymer.

Compounds expressed by equations (XII) through (XVII) may be used for another monomers. However, they are not limited to these compounds In order to accomplish the second object, a second invention of this application comprises a polyelectrolyte which contains at least a polymer of a compound expressed by an equation (XX).

$$
\begin{array}{c}
\text{(XX)} \\
\underset{R_1}{\overset{CH_2}{\underset{\parallel}{C}}}-\underset{\parallel}{\overset{}{C}}-O-\left[\underset{H_2}{\overset{H_2}{C}}-\underset{H_2}{\overset{H_2}{C}}-O-\underset{\parallel}{\overset{}{C}}-O\right]_n-\underset{H_2}{\overset{H_2}{C}}-\underset{H_2}{\overset{H_2}{C}}-O-\underset{\parallel}{\overset{}{C}}-\underset{R_2}{\overset{CH_2}{\underset{\parallel}{C}}}
\end{array}
$$

($R_1$ & $R_2$: H or $CH_3$ ($R_1$ may be same with or differ from $R_2$), n: integer ranging from 1 to 1,000)

Since the polyelectrolyte of the second invention contains the polymer of the compound expressed by the equation (XX), it provides a high ion conductivity and is superior in its electrochemical stability too.

(XII)

(XIII)

(XIV)

(XV)

(XVI)

(XVII)

In the equations (XII) through (XVII), v and w are integer of 1 or more.

(4) The polymeric compound is a polymer alloy of a polymer of at least one compound among those expressed by the equation (I) and the equation (II), with another polymeric compound. And, a weight content of the polymer of compounds expressed by the equation (I) and the equation (II) in the polymer alloy is larger than or equal to 50 wt %.

When the weight content of the polymer of compounds expressed by the equation (I) and the equation (II) in the polymer alloy is smaller than 50 wt %, structural characteristics of the compounds expressed by the equation (I) and the equation (II) do not present themselves as in case of characteristics of the polymer alloy.

Polyvinylidene fluoride, polyacrylonitrile, polyvinylalcohol, silicone resin and methacrylic resin etc. may be mentioned for another polymeric compounds. However, they are not limited to these compounds.

In order to accomplish the third object, a third invention of this application comprises an electrolyte material which is the compound expressed by the equation (XX), and a fourth invention of this application is an electrolyte material which is the polymer of the compound expressed by the equation (XX)

$$
\begin{array}{c}
\text{(XX)} \\
\underset{R_1}{\overset{CH_2}{\underset{\parallel}{C}}}-\underset{\parallel}{\overset{}{C}}-O-\left[\underset{H_2}{\overset{H_2}{C}}-\underset{H_2}{\overset{H_2}{C}}-O-\underset{\parallel}{\overset{}{C}}-O\right]_n-\underset{H_2}{\overset{H_2}{C}}-\underset{H_2}{\overset{H_2}{C}}-O-\underset{\parallel}{\overset{}{C}}-\underset{R_2}{\overset{CH_2}{\underset{\parallel}{C}}}
\end{array}
$$

($R_1$ & $R_2$: H or $CH_3$ ($R_1$ may be same with or differ from $R_2$), n: integer ranging from 1 to 1,000)

In order to accomplish the fourth object, a fifth invention of this application comprises a di(metha)-acrylic ester expressed by the equation (XX), and a sixth invention of this application comprises a di(metha)-acrylate polymer of the compound expressed by the equation (XX).

(XX)

($R_1$ & $R_2$: H or $CH_3$ ($R_1$ may be same with or differ from $R_2$), n: integer ranging from 1 to 1,000)

The compound expressed by the equation (XX) in the second through sixth inventions will be described hereunder. The compound expressed by the equation (XX) is a novel compound.

In this invention, the "(metha)-acrylic acid" means an acrylic acid or methacrylic acid, and the "(metha)-acrylate" means an acrylate or methacrylate.

The compound expressed by the equation (XX) is a di(metha)-acrylic ester. In the equation (XX), $R_1$ may be same with or differ from $R_2$. n is an integer ranging from 1 to 1,000, however, it preferably ranging from 5 to 500.

The di(metha)-acrylic ester expressed by the equation (XX) is an ester of the poly(1,3-propylene carbonate) expressed by the equation (XXI) with the (metha)-acrylic acid.

(XXI)

(n: integer ranging from 1 to 1,000)

The poly(1,3-propylene carbonate) is obtained by making react a 1,3-propanediol with a carbonyl component through the well-known method. Diester carbonates such as dimethyl carbonate, diethyl carbonate, diisopropyl carbonate, diphenyl carbonate, ethylene carbonate and propylene carbonate etc.; chloroformic esters such as chloroformic methyl, chloroformic ethyl and chloroformic phenyl etc.; and phosgene etc. may be used for the carbonyl component. It is desired to use such a carbonyl component at a ratio of 0.5 to 2 molar amount in relation to 1 mole of 1,3-propanediol. A number-average molecular weight of the poly(1,3-propylene carbonate) ranges from 200 to 100,000. It preferably ranges from 500 to 50,000, and more preferably ranges from 1,000 to 50,000.

As for manufacturing method of the di(metha)-acrylic ester, following methods (1) through (3) may be mentioned.

(1) A method in which the poly(1,3-propylene carbonate) and a (metha)-acrylic halide are condensed under existence of a base.

It is desired to use the (metha)-acrylic halide at a ratio of 0.5 to 10 equivalent in relation to a hydroxyl group of the poly(1,3-propylene carbonate). organic bases such as triethylamine, pyridine, dimethyl-amino-pyridine and diazabicycloundecene (DBU) etc.; inorganic bases such as sodium carbonate, potassium carbonate, sodium hydroxide and potassium hydroxide etc. may be used for the base. Generally, such a base is used at a ratio of 1 to 5 equivalent in relation to 1 mole of (metha)-acrylic halide. It is possible to carry out the reaction under non-solvent condition, but may be carried out under existence of a solvent inactive to the reaction. Hydrocarbon halides such as dichloromethane, chloroform, dichloroethane etc.; aromatic hydrocarbons such as benzene, toluene, xylene etc.; aliphatic hydrocarbons such as hexane, heptane, decane, cyclohexane etc.; ethers such as diethyl-ether, tetrahydrofuran (THF) etc. may be used for the inactive solvent. It is desired that a reaction temperature ordinarily ranges from −20 to 100° C., and preferably ranges from −5 to 50° C.

(2) A method in which the poly(1,3-propylene carbonate) and a (metha)-acrylic anhydride are condensed under existence of a catalyst.

It is desired to use the (metha)-acrylic anhydride at a ratio of 0.2 to 5 equivalent in relation to a hydroxyl group of the poly(1,3-propylene carbonate), and preferably at a ratio of 0.5 to 2 equivalent. Sulfuric acid, methane-sulfonic acid, p-toluene-sulfonic acid, pyridine and dimethyl-amino-pyridine etc. may be used for the catalyst. Generally, such a catalyst is used at a ratio of 0.01 to 0.5 equivalent in relation to (metha)-acrylic anhydride. It is possible to carry out this reaction under existence of the catalyst in the same way as the above (1). It is desired that a reaction temperature ordinarily ranges from −5 to 120° C., and preferably ranges from 25 to 100° C.

(3) A method in which the poly(1,3-propylene carbonate) and a (metha)-acrylic acid are condensed under existence of a acid catalyst.

It is desired to use the (metha)-acrylic acid at a ratio of 0.2 to 10 equivalent in relation to a hydroxyl group of the poly(1,3-propylene carbonate), and preferably at a ratio of 1 to 5 equivalent. Sulfuric acid, methane-sulfonic acid, p-toluene-sulfonic acid, etc. may be used for the acid catalyst. Generally, such an acid catalyst is used at a ratio of 0.01 to 0.5 equivalent in relation to the (metha)-acrylic acid. It is desirable to carry out the reaction under existence of a solvent which can be dehydrated azeotropically because water is produced under equilibrium condition. It is desired that a reaction temperature ranges from 25 to 180° C., and preferably ranges from 50 to 150° C.

When manufacturing the di(metha)-acrylic ester in the above methods (1) through (3), a polymerization prohibiting reagent may be used.

[Di(metha)-acrylate polymer]

The di(metha)-acrylate polymer is obtained by polymerizing the foregoing di(metha)-acrylate ester through irradiation of ultraviolet rays or radiation, or by applying heat. In this instance, the polymerizing reaction takes place in a structural unit of the (metha)-acrylate acid. This di(metha)-acrylate polymer can be used as the polyelectrolyte.

In case of the polymerization through the irradiation of ultraviolet rays, a photosensitizer can be used. Benzophenone, acetophenone, 2,2-dimethoxy-2-phenyl acetophenone etc. may be used for the photosensitizer.

In case of the polymerization by using heat, a thermal polymerization initiator can be used. Peroxides such as benzoyl peroxide, peroxy-dicarbonate etc.; azo compounds such as 2,2'-azobisisobutyronitrile etc.; nucleophilic reagents such as alkali metal etc.; electrophilic reagents such as Lewis acid etc. may be used for the thermal polymerization initiator by itself or in combination, according to a type of polymerization.

The di(metha)-acrylate polymer may be a single-polymer of di(metha)-acrylic ester, or a copolymer of two or more kinds of di(metha)-acrylic esters, or a copolymer of the di(metha)-acrylic ester with other monomers.

Vinyl monomer, vinylidene monomer, vinylene monomer etc. may be used for the other monomers for use in the copolymerization. Vinyl ester, vinyl ether, (metha)-acrylic ester, allyl ether, and allyl ester may preferably be used for the vinyl monomer. In concrete, (metha)-acrylic ethyl, (metha)-acrylic ethoxyethyl, (metha)-acrylic ethoxyethoxyethyl, poly(ethylene glycol)-(metha)-acrylate, allyl alcohol, vinyl acetate, stylene, □-methyl-stylene, vinyl chloride, vinylidene chloride, vinyl fluoride, vinylidene fluoride, acrylonitrile, cyanoacetic vinyl, allyl amine, isopropyl acrylic amide, vinylene carbonate, and maleic anhydride may be mentioned.

It is desirable that such another monomers are generally contained in the di(metha)-acrylic ester polymer at a weight percentage ranging from 0.1 to 90 wt %, and preferably ranging from 1 to 50 wt %.

The polyelectrolyte of this invention may contain a metal salt listed in Ia-group of periodic table. LiBr, LiI, $LiBF_4$, $LiPF_6$, $LiN(SO_2CF_3)_2$, NaBr, NaSCN, $NaClO_4$, KBr, KSCN, $KClO_4$ etc. may be mentioned for such a metal salt. When the metal salt is previously contained at time of polymerization of the di(metha)-acrylic ester, a polyelectrolyte uniformly containing the metal salt can be obtained with the di(metha)-acrylate polymer utilized as a matrix. A polyelectrolyte uniformly containing the metal salt can be obtained even when a liquid electrolyte dissolved with the metal salt is impregnated after polymerizing the di(metha)-acrylic ester.

The polyelectrolyte of this invention may contain non-aqueous solvent other than the metal salt listed in Ia-group of periodic table. The nonaqueous solvent is preferably used at a weight part of zero to 1,000, and more preferably at a weight parts of 100 to 700, in relation to 100 weight parts of the di(metha)-acrylate polymer. When the nonaqueous solvent is contained at time of polymerizing the di(metha)-acrylic ester, a polyelectrolyte containing the nonaqueous solvent can be obtained. The polyelectrolyte containing the nonaqueous solvent can be obtained even when the non-aqueous solvent is impregnated after polymerizing the di(metha)-acrylic ester. Ester carbonate or lactone may preferably used for the nonaqueous solvent. Ethylene carbonate, propylene carbonate, dimethyl carbonate, ethyl methyl carbonate, diethyl carbonate, dipropyl carbonate etc. may be used for the ester carbonate. γ-butyrolactone, δ-valerolactone, ε-caprolactone etc. may be used for the lactone.

Since the polyelectrolyte of this invention provides a high ion conductivity and is stable in electrochemical aspect, it can be used effectively for electrochemical elements such as a primary battery, a secondary battery, a condenser, an electrochromic indication element etc., and for a medical actuator etc. Especially, in a lithium ion secondary battery, the polyelectrolyte of this invention can be used as an alternative for an organic liquid electrolyte. In addition, the polyelectrolyte of this invention can be utilized as a binder for dispersing and fixing a powdery electrode reagent into a form of current collector.

A battery using the polyelectrolyte of this invention can be manufactured by forming the polyelectrolyte of this invention into a form of film and by sandwiching it between a positive electrode and a negative electrode.

In battery manufacturing processes including a process in which the liquid electrolyte is impregnated after forming a three-layer structure of the positive electrode, the separator and the negative electrode; in place of the liquid electrolyte, a process may be used wherein the polymerization is done after impregnating a solution composed of the di(metha)-acrylic ester, the metal salt listed in Ia-group of periodic table and the nonaqueous solution. According to this method, a remodeling of process can be restricted to a minimum.

The di(metha)-acrylic ester and the di(metha)-acrylate polymer of this invention may preferably used for a material of the polyelectrolyte. When such a polycarbonate-(metha)-acrylate polymer is used for a matrix of the polyelectrolyte of the lithium ion secondary battery, for example, a lithium ion secondary battery superior in its battery performance can be obtained.

BEST MODE FOR CARRYING OUT THE INVENTION

[Lithium Ion Mobility in Gel Electrolyte]

Figure 1:
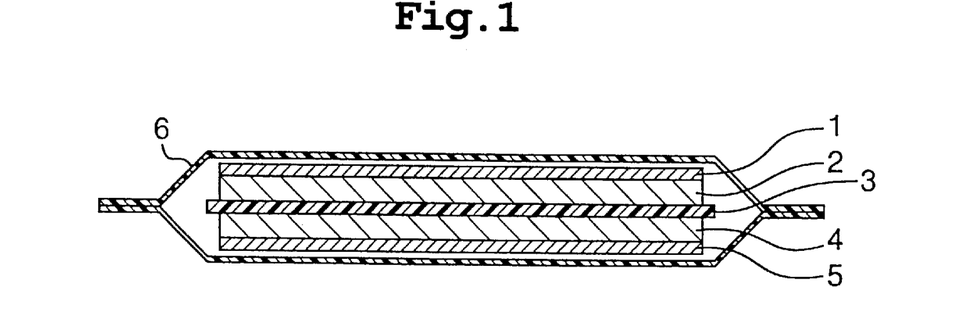
FIG. 1 is a sectional view of an evaluation cell for evaluating lithium ion mobilities in respective gel electrolytes of embodiment 1 and comparison embodiment 1.

Using the evaluation cell shown in FIG. 1, lithium ion mobilities were evaluated for both the gel electrolyte of this invention and a gel electrolyte using a crosslink polyalkylene oxide. Details are described in an embodiment 1 and a comparison embodiment 1. The evaluation cell shown in FIG. 1 is composed of current collectors 1 & 5 comprising stainless steel, lithium foils 2 & 4 of 4 $cm^2$, an external package 6 and an evaluated gel electrolyte 3. Evaluation was carried out in such a way that a current was flown between the lithium foil 2 and the lithium foil 4, and a voltage change between the two electrodes caused by a current change was measured. The measurement was done under an atmosphere of temperature of 20° C.

(Embodiment 1)

Macromonomer of weight-average molecular weights of about 4,600 (number-average molecular weights of about 1,600) expressed by an equation (XVIII), ethylene carbonate (EC) and γ-butyrolactone (γBL) were mixed with weight ratios of 21.2:34.8:44.0, and then $LiBF_4$ was dissolved in the mixture so as to realize 1 mol/litter. This mixed solvent was impregnated in a non-woven cloth which was in turn sandwiched between two films of poly(ethylene terephthalate) (PET), and the obtained piece was irradiated with electron beams to polymerize the macromonomer so that a gel electrolyte was made up. A thickness of this gel electrolyte was 150 μm. The non-woven cloth was used for a supporting member of the gel electrolyte in this instance, however, it is not necessary to use the non-woven cloth and a fine-porous film etc. To the foregoing mixed solvent, polymeric compounds such as the PVdF etc may be added.

(XVIII)

(Comparison embodiment 1)

Macromonomer of number-average molecular weights of about 8,000 expressed by an equation (XIX), EC and γBL were mixed with weight ratios of 21.2:34.8:44.0, and then LiBF$_4$ was dissolved in the mixture so as to realize 1 mol/litter. This mixed solvent was treated in the same way as the embodiment 1, so that a gel electrolyte was made up. A thickness of this gel electrolyte was 150 μm.

(XIX)

Figure 2:
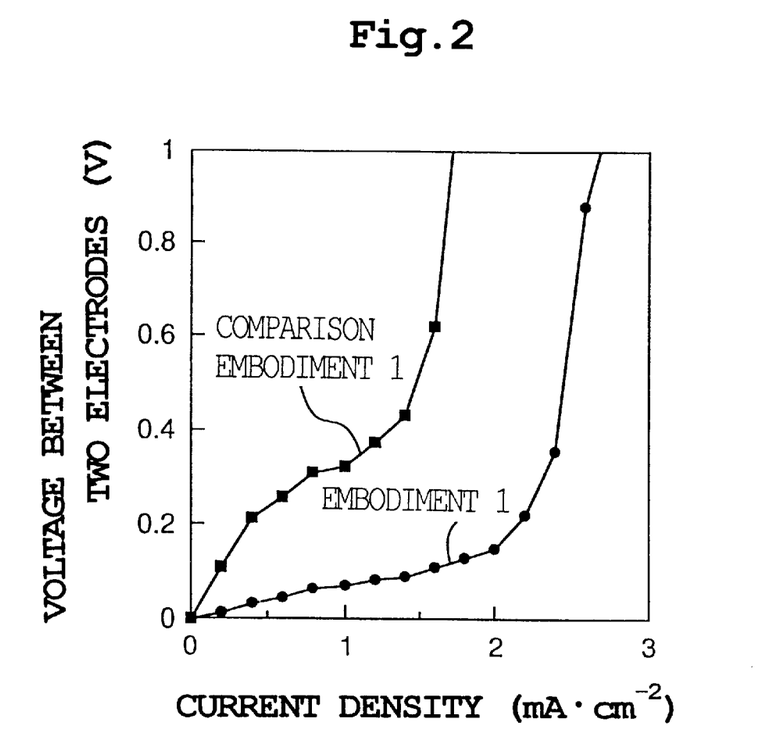
FIG. 2 is a graph showing evaluation results of lithium ion mobilities in respective gel electrolytes of embodiment 1 and comparison embodiment 1.

FIG. 2 shows evaluation results of lithium ion mobilities for respective gel electrolytes of the embodiment 1 and the comparison embodiment 1. Its axis of abscissa represents a current density and its axis of ordinate represents a voltage between two electrodes. The gel electrolyte of embodiment 1 provides a low voltage between two electrodes even at a high current density, as compared with the gel electrolyte of comparison embodiment 1. Such a difference between the voltage changes between two electrodes reflects the lithium ion mobilities, and suggests that the lithium ion mobility is larger in the gel electrolyte of embodiment 1 than in those of the comparison embodiment 1. Consequently, it can be expected that charging and discharging at higher current density become possible in a battery using the gel electrolyte of embodiment 1.

[Discharge Property of Battery]

Figure 3:
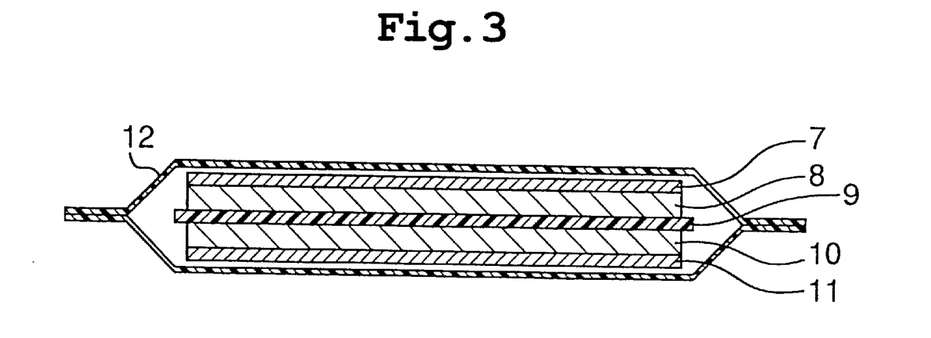
FIG. 3 is a sectional view of a battery using the gel electrolyte.

Discharge properties were evaluated for a battery using the gel electrolyte of embodiment 1 and for a battery using the gel electrolyte of comparison embodiment 1. Details are described in an embodiment 2 and a comparison embodiment 2. FIG. 3 is the sectional view of the battery using the gel electrolyte. This battery is composed of a current collector 7 comprising aluminum, a positive electrode 8, a current collector 11 comprising copper, a negative electrode 10, an external package 12 and a gel electrolyte 9.

(Embodiment 2)

A battery having a battery capacity of about 9.45 mAh shown in FIG. 3 was made up using the gel electrolyte of embodiment 1. A thickness of the gel electrolyte 9 was 30 μm. A positive electrode 8 was composed of an active material of LiCoO$_2$, an acetylene black (AB) forming a conductive agent, a PVdF forming a binder, and a gel electrolyte. A negative electrode 10 was composed of a carbon, a PVdF forming a binder and a gel electrolyte.

(Comparison Embodiment 2)

In the same way as the embodiment 2, except that the gel electrolyte of comparison embodiment 1 was used, a battery having a battery capacity of about 9.45 mAh shown in FIG. 3 was made up.

Figure 4:
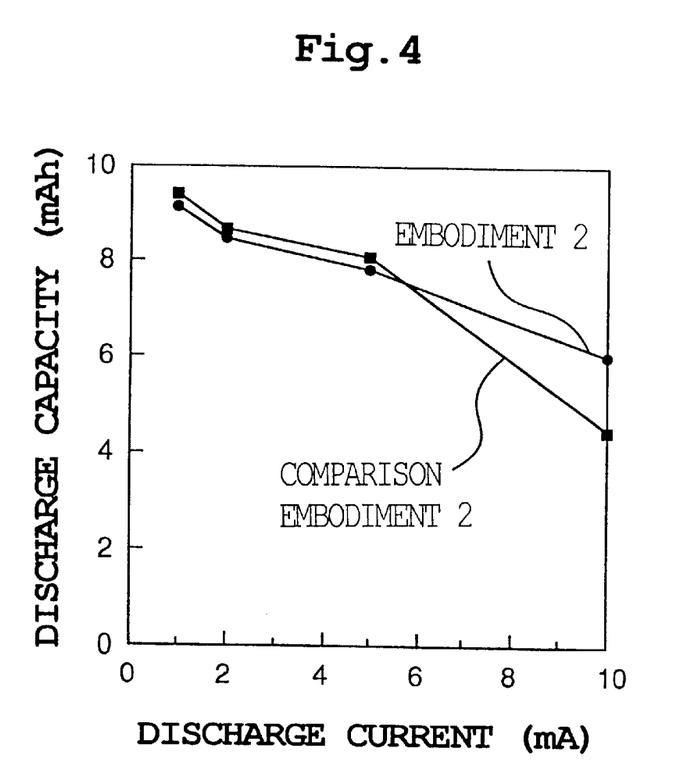
FIG. 4 is a graph showing results of discharge tests for respective batteries of embodiment 2 and comparison embodiment 2.

FIG. 4 shows results of discharge tests for respective batteries of an embodiment 2 and a comparison embodiment 2. Its axis of abscissa represents a discharge current and its axis of ordinate represents a discharge capacity. As seen from FIG. 4, at a discharge current of up to 5 mA, approximately similar discharge capacities were obtained for both the batteries of embodiment 2 and comparison embodiment 2. At a discharge current of 10 mA, however, a difference in discharge capacity was produced between the two batteries. It can be understood from this fact that the battery of embodiment 1 is superior in its high-rate characteristic as compared with the battery of comparison embodiment 2.

(Embodiment 3)

This embodiment relates to the diacrylic ester. 1,066 grams of 1,3-propanediol and 1,514 grams of dimethyl carbonate and 5.41 grams of 28% sodium methoxide methanol solution for use in a catalyst were mixed in a glass reaction vessel equipped with a stirrer, a thermometer and a rectification tower etc. The mixture was held at 95° C. under normal pressure for two hours. After that, its temperature was raised up to 150° C. spending five hours, and further it was heated at 150° C. for four hours. In this instance, methanol produced during the reaction was removed.

In the next stage, the mixture was held at a temperature of 150 through 155° C. under a reduced pressure of 5 mmHg and 210 g of 1,3-propanediol produced in the polymerizing reaction were removed, so that 1,127 grams of poly(1,3-propylene carbonate) were obtained as a consistent oil. A number-average molecular weights of the obtained poly(1,3-propylene carbonate) was 2,400 when measured by a gel permeation chromatography.

Thereafter, 90 grams of poly(1,3-propylene carbonate) and 11.3 grams of triethylamine and 100 ml of 1,2-dichloroehthane were mixed in a glass reaction vessel equipped with a stirrer, a thermometer and a dropping funnel etc., and the mixture was cooled down to 5° C. 9.3 grams of chloride acrylate was dropped into the mixture from the dropping funnel spending a time of 10 minutes, and the mixture was stirred at 5° C. for one hour. Then its temperature was raised to a room temperature and the mixture was further stirred at the room temperature for two hours.

Figure 5:
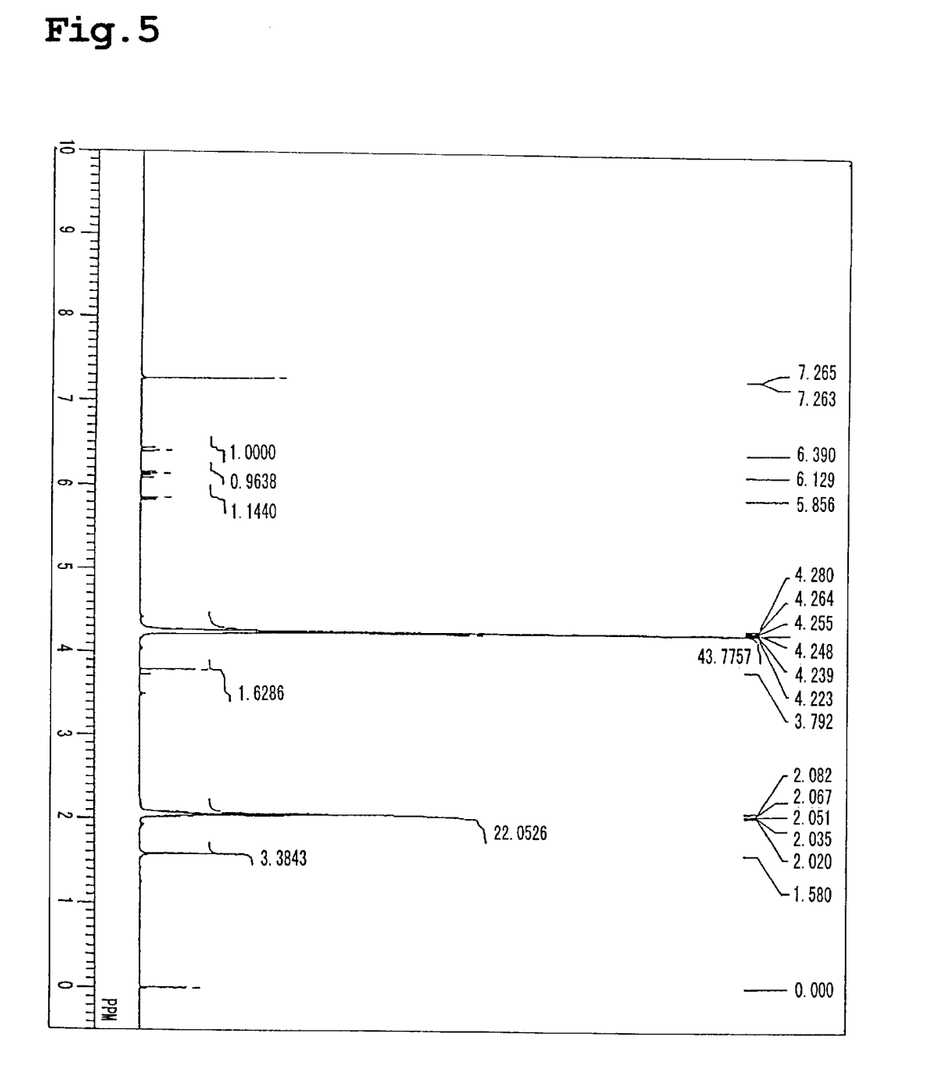
FIG. 5 is a $^1$H-NMR chart of the diacrylic ester.

The reacted solution was filtered, the filtered solution was washed by saturated salt water and dried by nonaqueous magnesium sulfate. The prepared product was condensed to obtain a target product: 84 grams of diacrylic ester in a form of light-yellow consistent oil. A $^1$H-NMR chart of the obtained diacrylic ester is shown in FIG. 5.

(Embodiment 4)

This embodiment relates to the dimethacrylic ester. 90 grams of poly(1,3-propylene carbonate) synthesized in the embodiment 3 and 11.3 grams of triethylamine and 100 ml of 1,2-dichloroehthane were mixed in a glass reaction vessel equipped with a stirrer, a thermometer and a dropping funnel etc., and the mixture was cooled down to 5° C. 10.7 grams of chloride methacrylate was dropped into the mixture from the dropping funnel spending a time of 10 minutes, and the mixture was stirred at 5° C. for one hour. Then its temperature was raised to a room temperature and the mixture was further stirred at the room temperature for two hours.

Figure 6:
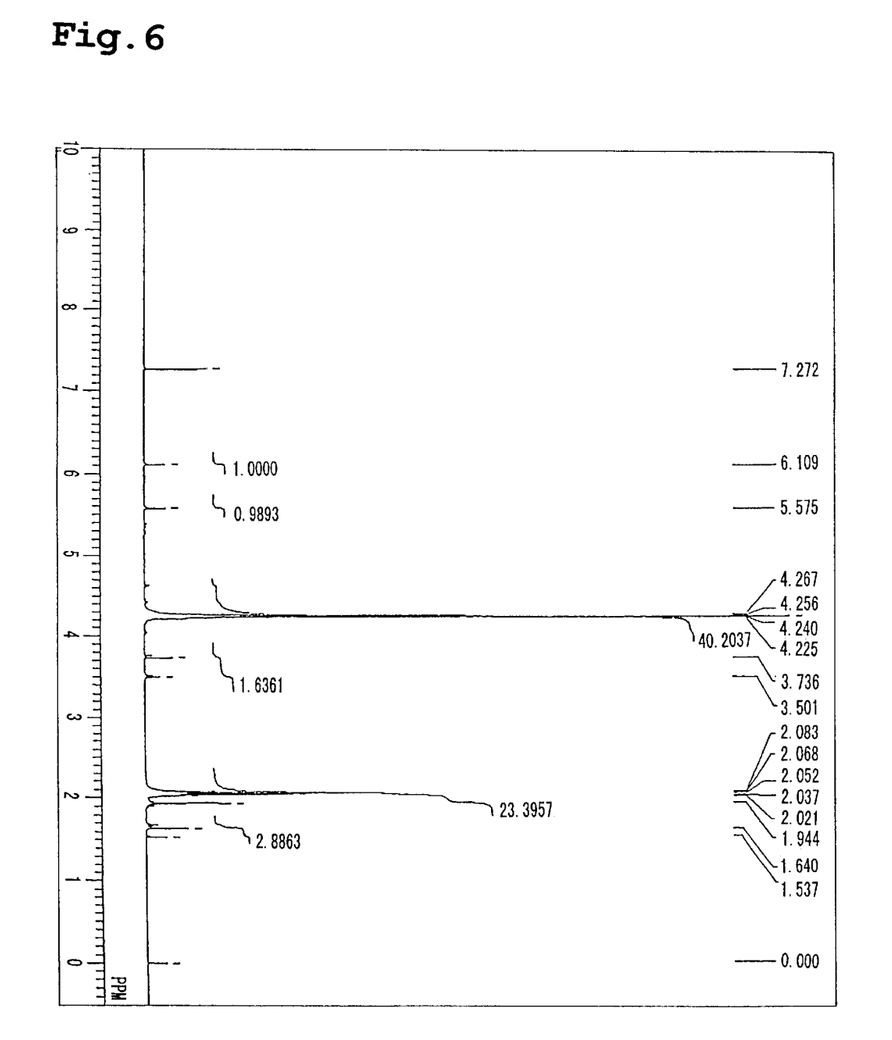
FIG. 6 is a $^1$H-NMR chart of the dimethacrylic ester.

The reacted solution was filtered, the filtered solution was washed by saturated salt water and dried by nonaqueous magnesium sulfate. The prepared product was condensed to obtain a target product: 87 grams of dimethacrylic ester in a form of light-yellow consistent oil. A $^1$H-NMR chart of the obtained dimethacrylic ester is shown in FIG. 6.

(Embodiment 5)

This embodiment relates to the polyelectrolyte.

20.0 weight parts of ester diacrylate manufactured in the embodiment 3 were mixed with 80.0 weight parts of liquid electrolyte, the mixture solution was cast on a glass plate and irradiated with ultraviolet rays from a position 7 cm above a substrate, and polymerized and hardened, under an atmosphere of inert gas, so that a polyelectrolyte having a thickness of about 0.5 mm was manufactured. The abovementioned liquid electrolyte was prepared in such a way that ethylene carbonate was mixed with propylene carbonate in the equal amount (weight ratio) and LiPF$_6$ was dissolved in this mixture at a concentration of 1 mol/litter. The ultraviolet rays were irradiated using an ultraviolet ray irradiation device (Type: UIS-25102, Maker: Ushio Electric Co.) equipped with an optical fiber unit (Type:SF-101Q).

The prepared polyelectrolyte was punched into a disc having a diameter of 10 mm to make up a test piece, and this test piece was subjected to measurements of ion conductivity and voltage resistance.

(1) Measurement of Ion Conductivity

The test piece was sandwiched between electrodes of conductivity measuring holder. The electrodes were controlled at 25° C. by a Peltier element, under this state a complex impedance was measured (measurement voltage: 10 mV) and analyzed by using an impedance analyzer (Type: HP4285A, Maker: Hewlett Packard). The ion conductivity was 2.83 S/cm$^2$.

Accordingly, the polyelectrolyte of this embodiment provides a high ion conductivity.

(2) Measurement of Voltage Resistance

Using Pt(electrode area: 0.5 cm$^2$) as a working electrode, using Li(electrode area: 4 cm$^2$) as a counter electrode, and using Li (electrode area: 0.5 cm$^2$) as a reference electrode; a voltage resistance of the test piece was measured by means of Cyclic Voltammetry method utilizing a Potentiostat (Trade name: "Solartron 1286", Maker: Solartron). The voltage resistance was 5.6 V.

Accordingly, the polyelectrolyte of this embodiment is superior in its electrochemical stability.

(Embodiment 6)

A polyelectrolyte was manufactured in the same way as the embodiment 5, except that the dimethacrylic ester manufactured in the embodiment 4 was used in place of the ester diacrylate. The prepared polyelectrolyte was subjected to measurements of ion conductivity and voltage resistance in the same way as the embodiment 5. The ion conductivity was 3.20 mS/cm$^2$ and the voltage resistance was 4.5 V. Accordingly, the polyelectrolyte of this embodiment provides a high ion conductivity and is superior in its electrochemical stability.

INDUSTRIAL USEFUL FIELD

This application can provide a lithium battery superior in its reliability, safety and charge/discharge characteristics, and can provide a polyelectrolyte effectively used for an electrochemical element. Therefore, it is very useful especially in the battery industry.

What is claimed is:

1. A lithium battery comprising:
   a positive electrode;
   a negative electrode; and
   a gel electrolyte, wherein the gel electrolyte is composed of at least an ester-group or ether-group aprotic polar solvent, a lithium salt and a polymeric compound, and the polymeric compound comprises a polymer of at least one compound among those expressed by formula (I) and formula (II):

$$X{-}[{-}({-}C(=O){-}O{-}R_1{-}O{-})_k({-}C(=O){-}O{-}R_2{-}O{-})_m{-}A]_n \quad (I)$$

$$A{-}(O{-}R_3{-}O{-}C(=O){-})_r(O{-}R_4{-}O{-}C(=O){-})_s O{-}R_4{-}O{-}A \quad (II)$$

wherein:
k is zero or more,
m is 1 or more,
R$_1$ is C$_p$H$_{2p}$,
R$_2$ is C$_q$H$_{2q}$,
p≠q,
p and q are integers of 1 or more,
A is CH$_2$=CH—CO— or CH$_2$=C(CH$_3$)—CO—,
X is an n-valent combination group, wherein n is an integer ranging from 1 to 4,
r is zero or more,
s is 1 or more,
R$_3$ is C$_t$H$_{2t}$,
R$_4$ is C$_u$H$_{2u}$,
t≠u,
t and u are integers of 1 or more, and u≠2 when r=0.

2. A lithium battery as set forth in claim 1, in which a number-average molecular weight of the compound expressed by the formula (I) ranges from 160 to 100,000.

3. A lithium battery as set forth in claim 1, in which a number-average molecular weight of the compound expressed by the formula (II) ranges from 228 to 100,000.

4. A lithium battery as set forth in claim 1, in which the polymeric compound comprises a copolymer of at least one compound among those expressed by the formula (I) and the formula (II), with an another monomer, and
   a content of the compound expressed by the formula (I) and the formula (II) in the copolymer is larger than or equal to 50 wt %.

5. A lithium battery as set forth in claim 1, in which the polymeric compound comprises a polymer alloy of at least a polymer of one compound among those expressed by the formula (I) and the formula (II), with an another polymeric compound, and
   a content of the polymer of the compound expressed by the formula (I) and the formula (II) in the polymer alloy is larger than or equal to 50 wt %.

6. A polyelectrolyte containing at least a polymer of a compound expressed by an formula (XX):

$$(XX)$$

$$R_1{-}C(=CH_2){-}C(=O){-}O{-}[CH_2{-}CH_2{-}O{-}C(=O){-}O]_n{-}CH_2{-}CH_2{-}O{-}C(=O){-}C(=CH_2){-}R_2$$

wherein
R$_1$ and R$_2$ are H or CH$_3$, wherein R$_1$ may be same with or differ from R$_2$, n is an integer ranging from 1 to 1,000.

7. An electrolyte material comprising a compound expressed by an formula (XX):

(XX)

wherein $R_1$ and $R_2$ are H or $CH_3$ and $R_1$ may be same with or differ from $R_2$, n is an integer ranging from 1 to 1,000.

8. An electrolyte material comprising a polymer of a compound expressed by an formula (XX):

(XX)

wherein $R_1$ and $R_2$ are H or $CH_3$ and $R_1$ may be same with or differ from $R_2$, n is an integer ranging from 1 to 1,000.

9. A di(metha)-acrylic ester expressed by an formula (XX):

(XX)

wherein $R_1$ and $R_2$ are H or $CH_3$ and $R_1$ may be same with or differ from $R_2$, n is an integer ranging from 1 to 1,000.

10. A di(metha)-acrylate polymer forming a polymer of a compound expressed by an formula (XX):

(XX)

wherein $R_1$ and $R_2$ are H or $CH_3$ and $R_1$ may be same with or differ from $R_2$, n is an integer ranging from 1 to 1,000.

* * * * *